(12) United States Patent
Abboud

(10) Patent No.: US 9,039,417 B2
(45) Date of Patent: May 26, 2015

(54) JAW IMPLANT

(76) Inventor: Marcus Abboud, Setauket, NY (US)

( * ) Notice: Subject to any disclaimer, the term of this patent is extended or adjusted under 35 U.S.C. 154(b) by 36 days.

(21) Appl. No.: 13/612,889

(22) Filed: Sep. 13, 2012

(65) Prior Publication Data

US 2013/0065198 A1   Mar. 14, 2013

(30) Foreign Application Priority Data

Sep. 14, 2011 (EP) ..................................... 11181245

(51) Int. Cl.
A61C 8/00 (2006.01)

(52) U.S. Cl.
CPC .............. A61C 8/0022 (2013.01); A61C 8/0053 (2013.01)

(58) Field of Classification Search
CPC ............................ A61C 8/0018; A61C 8/0022
USPC ....................................... 433/172–176, 201.1
See application file for complete search history.

(56) References Cited

U.S. PATENT DOCUMENTS

| 4,713,004 | A | 12/1987 | Linkow et al. | |
| 5,954,504 | A * | 9/1999 | Misch et al. | 433/174 |
| 6,672,872 | B2 * | 1/2004 | Cottrell | 433/173 |
| 2003/0031982 | A1 * | 2/2003 | Abarno | 433/173 |
| 2003/0068600 | A1 * | 4/2003 | Ellison | 433/174 |
| 2006/0194170 | A1 * | 8/2006 | Wohrle et al. | 433/173 |
| 2007/0037123 | A1 * | 2/2007 | Mansueto et al. | 433/173 |
| 2007/0099153 | A1 * | 5/2007 | Fromovich | 433/174 |
| 2008/0261175 | A1 * | 10/2008 | Hurson | 433/173 |
| 2011/0027756 | A1 | 2/2011 | Benatouil et al. | |

FOREIGN PATENT DOCUMENTS

| EP | 0 198 306 A2 | 10/1986 |
| EP | 0 449 334 A1 | 10/1991 |

* cited by examiner

Primary Examiner — Cris L Rodriguez
Assistant Examiner — Hao D Mai
(74) Attorney, Agent, or Firm — Norman B. Thot

(57) ABSTRACT

A jaw implant includes an implant body comprising a top end, a base end, an axial line, an acute-angled long side, an obtuse-angled short side, a body core. An oval opening disposed at the top end comprises an opening edge lying in an opening plane inclined with an angle of inclination of 75° to 45° with respect to the axial line so that the implant body has an axial length on the acute-angled long side longer than on the obtuse-angled short side. An external thread structure comprises a lead comprising a lower side facing the base end, an upper side facing the top end, and a wedge angle disposed between the upper side and the lower side. A bisecting line of the wedge angle and the axial line of the implant body form a tilt angle which is smaller on the acute-angled long side than on the obtuse-angled short side.

19 Claims, 4 Drawing Sheets

JAW IMPLANT

CROSS REFERENCE TO PRIOR APPLICATIONS

Priority is claimed to European Patent Application No. EP 11181245.9, filed Sep. 14, 2011. The entire disclosure of said application is incorporated by reference herein.

FIELD

The present invention relates to a dental jaw implant for supporting an implant abutment.

BACKGROUND

A dental jaw implant is that part of a dental implant structure that is implanted directly into the jaw of a patient in order to support an implant abutment.

A straight configuration is generally intended for the overall implant structure, i.e., the jaw implant and the implant abutment are on the same axial line. However, a patient's jaw bone, the nerve tracts extending therein, and other marginal conditions do not always allow the jaw implant to always be implanted into the jaw bone approximately transversely to the occlusal plane. If the jaw implant is implanted into the jaw bone at an angle with respect to the occlusal plane, the implant abutment must be fixed to the jaw implant at a corresponding angle.

A dental implant structure with an implant abutment inclined with respect to the jaw implant is described, for example, in EP 0 449 334 A1, where the implant body has an opening at the top end whose opening plane is typically inclined under an angle of inclination from 75° to 45° with respect to the axial line. A problematic aspect of inclined implant abutments is the non-axial introduction of force into the jaw implant, for which, in particular, the conventional threads on the outer side of the implant body are not well suited.

SUMMARY

An aspect of the present invention is to provide a jaw implant for an inclined or bent implant structure with an improved support in the jaw of a patient.

In an embodiment, the present invention provides a jaw implant which includes an implant body comprising a top end configured to fasten a prosthetic implant abutment. A base end is configured to be inserted into a patient's jaw. An axial line. An acute-angled long side. An obtuse-angled short side. A body core. An oval opening is disposed at the top end. The oval opening comprises an opening edge lying in an opening plane which is inclined with an angle of inclination of 75° to 45° with respect to the axial line so that the implant body has an axial length on the acute-angled long side which is longer than on the obtuse-angled short side. An external thread structure is configured to thread the implant body into a jaw bone. The external thread structure comprises a lead which extends on a continuous screw line with a constant pitch around the axial line and which is configured to protrude laterally from the body core. The lead has a wedge-like shape and comprises a lower side facing the base end, an upper side facing the top end, and a wedge angle disposed between the upper side and the lower side. A bisecting line of the wedge angle and the axial line of the implant body form a tilt angle which is smaller on the acute-angled long side than on the obtuse-angled short side.

BRIEF DESCRIPTION OF THE DRAWINGS

The present invention is described in greater detail below on the basis of embodiments and of the drawings in which.

DETAILED DESCRIPTION

Figure 1:
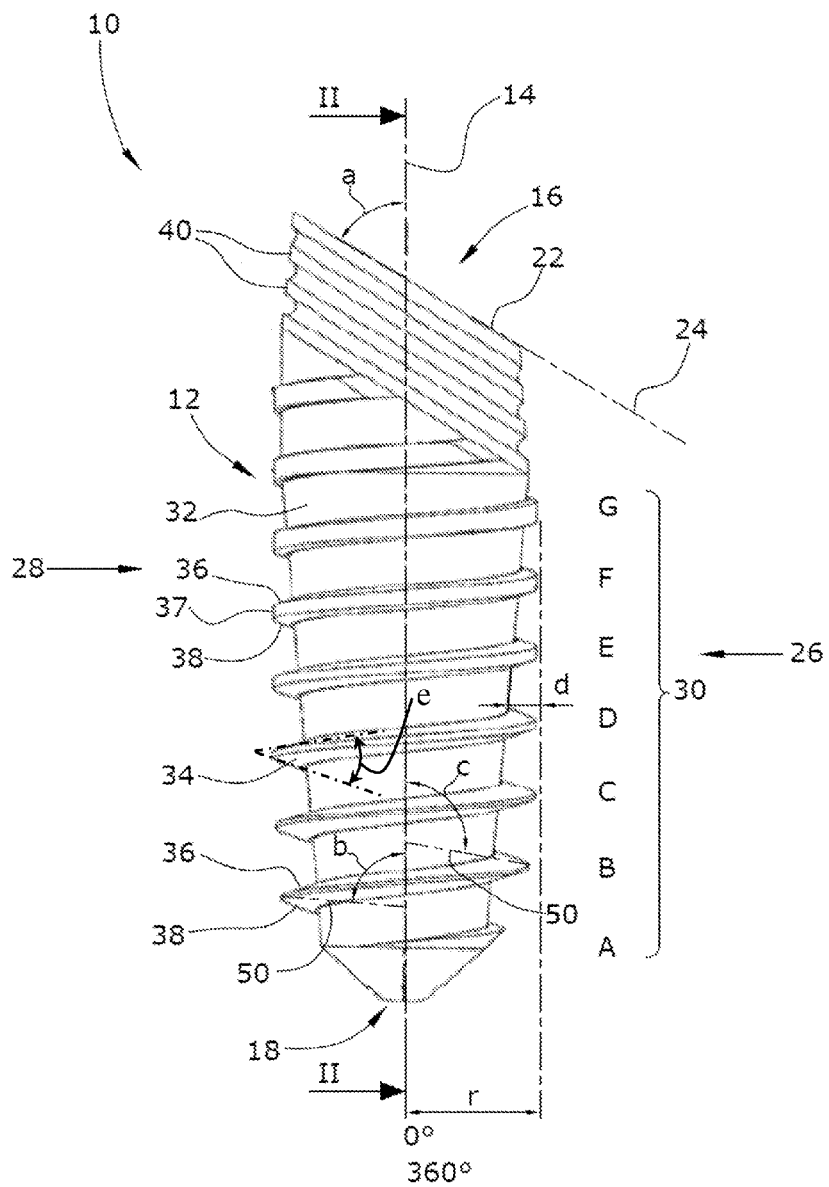
FIG. 1 shows a side elevational view of a jaw implant with an inclined opening plane.

The jaw implant of the present invention comprises an implant body which, seen in the axial direction, has a top end for fastening the prosthetic implant structure thereto, and has a base end at its other axial end for insertion into the jaw of a patient. At the top end, the implant body has an oval opening with an opening edge, the opening edge lying in an opening plane inclined under an inclination angle from 75° to 45° with respect to the axial line of the implant body so that the opening plane is inclined under an angle from 15° to 45° with respect to the transversal plane of the implant body.

The implant body thus terminates in a chamfer at its top end so that the implant abutment can be set on the implant body under the inclination angle under which the opening plane is inclined with respect to the transversal plane of the implant body. Since the implant body is chamfered at the top end, it has one side along its circumference, where the axial extension of the body is maximal, and a side opposite that side, where the axial extension of the body is minimal. The angle included by the opening plane and the circumferential surface of the implant body is acute at the long side and obtuse at the short side.

On the outer side, the implant body has a thread structure for screwing the implant body into a jaw bone. In practice, a thread structure is particularly advantageous, on the one hand, for the insertion of the implant body into the jaw of a patient and, on the other hand, for the ingrowth of the implant body into the jaw of a patient.

The thread structure is substantially formed by a lead that projects laterally from a body core and extends in a continuous screw line with a constant pitch. The inclination of the lead with respect to the axial line is not constant along the circumference, but varies, respectively, between two extremes over 360° of circumference. Depending on its rotational position along the circumference of the implant body, the lead thus tilts about a zero position respectively situated between the long side and the short side, i.e., at the transition from the long side to the short side.

The lead is wedge-shaped in cross section and comprises a lower side facing to the base end and an upper side facing to the top end. The top end and the bottom end of the lead include a wedge angle between them. On the top end side, the bisecting line of the wedge angle forms a tilt angle with the axial line of the implant body, which tilt angle is smaller on the long side of the implant body than on the short side of the implant body. On the long side of the implant body, the lead is tilted more towards the top end than on the short side of the implant body. In particular, the lower side of the lead is inclined more towards the top end on the long side than on the short side. The parallelism of the lower side of the lead relative to the opening plane is thereby greater than it would be the case if the lead had a constant inclination all along the circumference with respect to the axial line of the implant body. Overall, on the long side of the implant body, the lower sides of the lead are each as close as possible to a right angle with respect to the force introduction axis which extends perpendicularly to the opening plane. The force introduced into the implant body via the opening plane can thus be transmitted to the jaw bone over a larger area by the lead on the long side than would be the case if the inclination of the lower side of the lead were constant along the circumference. The same is true, correspondingly, for the upper side of the lead on the short side of the implant body. On the short side, the upper side of the lead is tilted, as compared with the long side, such that the upper side is arranged as parallel as possible with respect to the opening plane. It is thus possible in this region to introduce torques or the pressure forces resulting therefrom into the jaw of a patient over a surface area as large as possible.

In an embodiment of the present invention, the bisecting line of the wedge angle of the lead and the implant body axial line can, for example, include, at the top side, a tilt angle b smaller than 90° on the long side, and, on the short side, include a tilt angle c larger than 90°. The bisecting line of the wedge angle of the lead tilts between the long side and the short side between c=105° and b=75°, for example. For a typical inclination angle of the opening plane of 30°, for instance, and a wedge angle also of 30°, the lower aides in the long side and the top sides on the short side are each approximately parallel to the opening plane. While this geometry could basically also be obtained with a lead having a constant tilt angle over the circumference, this lead would have a rather large wedge angle, e.g., 60° in the present case, so that such a lead would take relatively much space in the axial direction. By tilting or twisting the lead along the circumference, the wedge angle of the lead can be reduced and the pitch can be decreased so that the number of lead sections on the long side and on the short side can be increased correspondingly. The wedge angle of the lead can, for example, be smaller than twice the inclination of the opening plane with respect to the transversal plane.

In an embodiment of the present invention, the wedge angle of the lead can, for example, be constant over the circumference. If the lead depth were also constant, the cross section profile of the lead would thus not change for a plurality of lead turns.

In an embodiment of the present invention, the upper side and/or the lower side of the lead can, for example, be planar. A planar configuration of the upper and lower sides of the lead provides the largest possible support surface for force transmission between the implant body and the jaw of a patient. In an embodiment of the present invention, the implant body core can, for example, taper down to the base end. The lead depth of the lead can, for example, increase to a similar or the same extent towards the base end so that, for example, the outer radius of the implant body is constant for a plurality of turns, i.e., the nominal diameter of the respective thread section is constant.

In an embodiment of the present invention, the implant body can, for example, have at least one closed raised support ring in its top end, whose ring plane is parallel to the opening plane. This allows for a good support of the implant on the jaw of a patient in the edge portion of the opening plane.

In an embodiment of the present invention, the lead can, for example, be of a trapezoidal cross-sectional shape, which does not necessarily mean a symmetric trapezoid.

The following is a detailed description of an embodiment of the present invention with reference to the Figures.

The Figures illustrate an angled jaw implant 10 formed by an implant body 12 of titanium. The jaw implant 10 may be screwed into an appropriately pre-drilled jaw of a patient and be implanted in this manner. A prosthetic implant structure can be fastened on the implanted jaw implant 10.

The implant body 12 has a top end 16 for fastening the implant abutment and a base end 18, with which the implant body 12 first penetrates into the jaw of a patient as the implant is screwed thereinto.

At the top end 16 the implant body 12 has an oval opening 20 with a correspondingly oval opening edge 22. Below the oval opening 20, a fastening structure is provided in the implant body 12 by means of which the implant abutment can be fastened to the implant body 12. The oval opening edge 22 lies in an opening plane 24 that is inclined under an inclination angle a of 60°, for example, with respect to the axial line 14 of the implant body 12. Due to the inclination of 30° of the opening plane 24 with respect to the transversal plane of the implant body 12, the axial length of the implant body differs on different circumferential sides. The acute-angled long side 28 is the side on which the opening plane 24 forms the most acute angle with the circumferential surface of the implant body 12. The obtuse-angled short side 26 is the side on which the opening plane 24 includes an obtuse angle with the circumferential surface of the implant body 12. On the acute-angled long side 28 the implant body 12 is longer than on its opposite obtuse-angled short side 26.

The implant body 12 has a thread structure 30 formed by a lead 34 of a constant pitch, the lead 34 extending along a screw line around a body core 32 from which it protrudes laterally. The lead 34 makes approximately seven full turns that are identified by the letters A to G in FIG. 1. The lead 34 is wedge-shaped in cross section as can be seen, in particular, in FIG. 2. The wedge angle e of the lead 34, with its wedge-shaped cross section, is approximately 30°. The lead 34 has a planar lower side 38 facing towards the base end 18 and a planar upper side 36 facing towards the top end 16. Depending on the lead depth d, the lead 34 ends in a lead top surface 37, with the lead top surfaces 37 of a plurality of turns B to G lying in a single cylinder plane.

Figure 2:
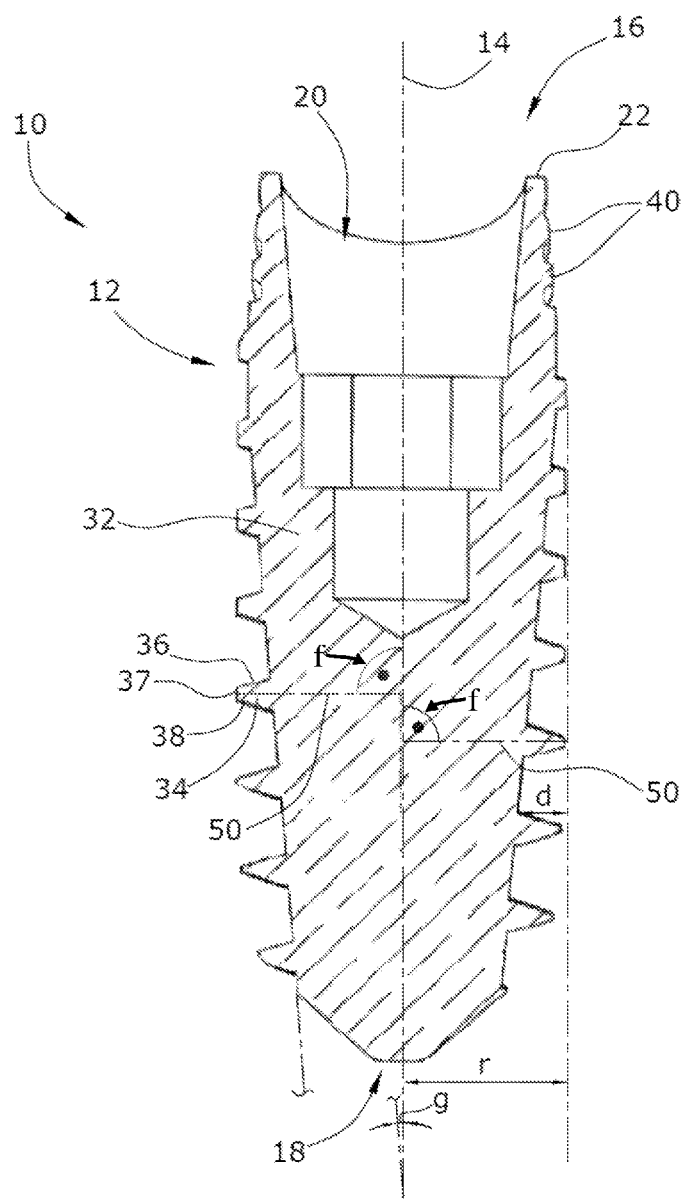
FIG. 2 shows a longitudinal section through the jaw implant of FIG. 1 along the sectional plane II-II.
Figure 3:
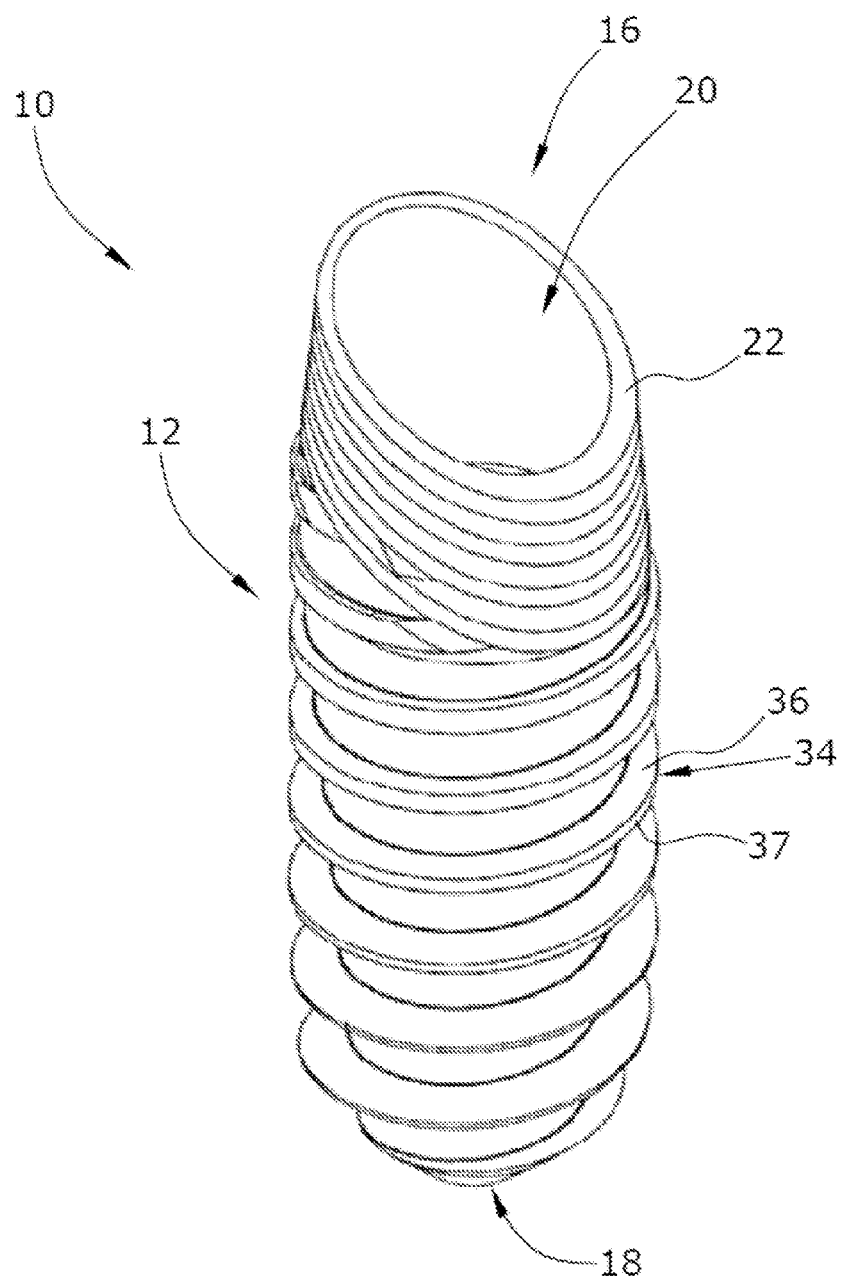
FIG. 3 shows a perspective view of the jaw implant of FIG. 1.

The bisecting line 50 of the wedge angle e of the lead 34 is not under a constant angle to the axial line 14, but changes periodically in each turn. On the acute-angled long side 28, bisecting line 50 of the lead 34 is inclined under an angle b of 75° with respect to the axial line 14. On the obtuse-angled short side 26, the bisecting line 50 of the lead 34 is inclined under an angle c of 105° with respect to the axial line 14. Between these two extremes, the angle of the lead 34 to the axial line 14 changes continuously so that the angle f is exactly 90° at the two intermediate positions between the acute-angled long side 28 and the obtuse-angled short side 26, as illustrated in FIG. 2.

In the region of the thread structure 30, the body core 32 is not cylindrical, but is formed to taper conically towards the base end 18 under a cone angle g. The lead depth d increases towards the base end 18 to the extent that the outer radius of the body core 32 decreases towards the base end 18, so that the outer radius r of the implant body 12 as a whole is virtually constant for several turns C to G, and the lead top surfaces 37 of several turns C to G describe a cylinder.

While the base of the wedge-shaped lead 34 remains unchanged over all turns A to G, the tip of the wedge-shaped lead 34 is cut off ever more as the lead depth d decreases so that, in the top-side part of decreased lead depth d, the lead 34 has a trapezoidal cross section where the axial height of the lead top surface 37 constantly increases towards the top end.

Figure 4:
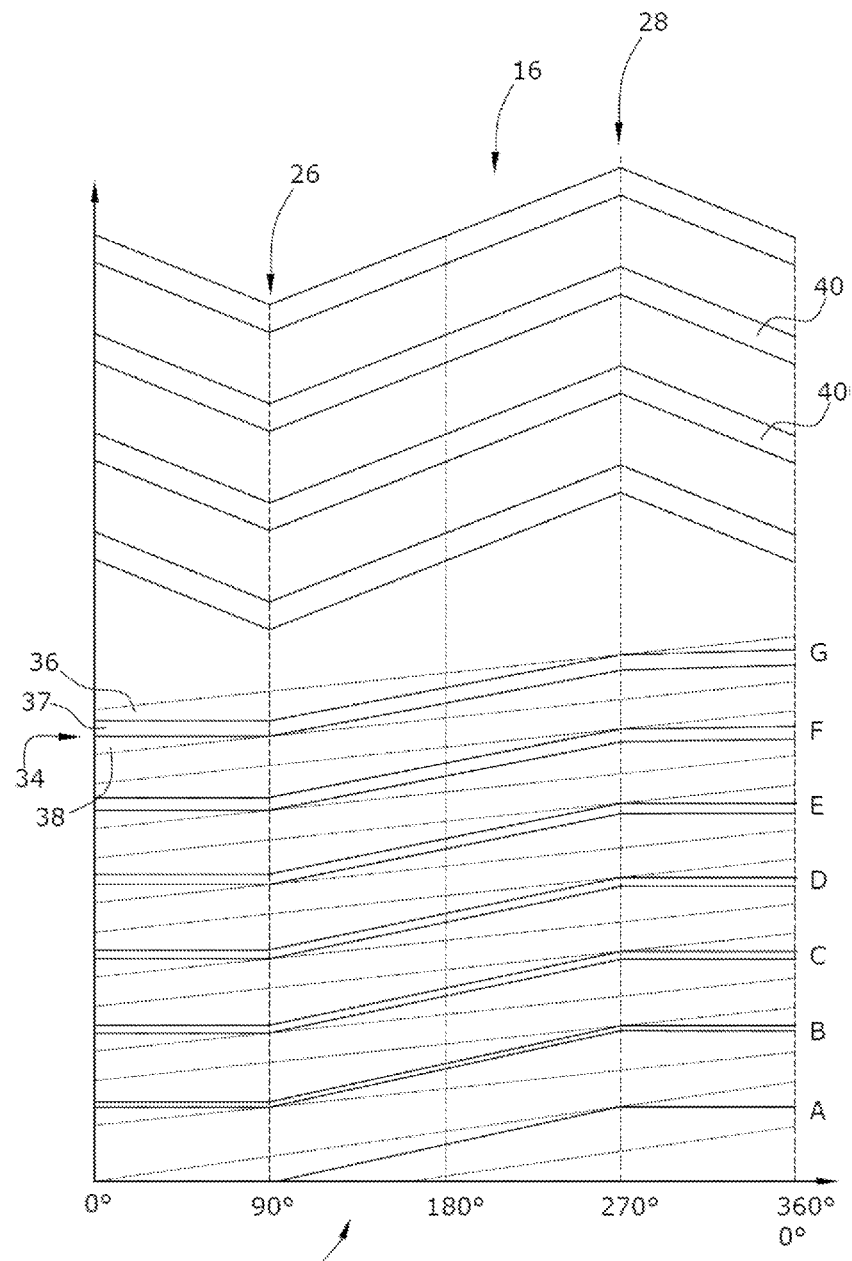
FIG. 4 shows a schematic development of the thread of the jaw implant of FIG. 1.

The path of the lead 34 along the circumference becomes clear with reference to FIG. 4 that shows a schematic development of the circumference of the implant body. The development illustrated is distorted, since the conicity of the implant body 12 has been ignored and the implant body is illustrated as if it were cylindrical over its entire length. Further, in the development illustrated in FIG. 4, the transitions of the lead 34 and the support rings 40 on the obtuse-angled short side 26 and the acute-angled long side 28 are illustrated as being abrupt, while they are actually arcuate. The development clearly shows how the lead 34 is tilted between the obtuse-angled short side 26 and the acute-angled long side 28, whereby the lead top surface 37 oscillates between the upper end and the lower end of the projection of the lead base. Further, the element clearly shows that the axial height of the lead top surfaces 37 constantly decreases towards the base end 18.

The present invention is not limited to embodiments described herein; reference should be had to the appended claims.

What is claimed is:

1. A jaw implant comprising an implant body comprising
   a top end configured to fasten a prosthetic implant abutment;
   a base end configured to be inserted into a patient's jaw;
   an axial line;
   an acute-angled long side;
   an obtuse-angled short side;
   a body core;
   an oval opening disposed at the top end, the oval opening comprising an opening edge lying in an opening plane which is inclined with an angle of inclination of 75° to 45° with respect to the axial line so that the implant body has an axial length on the acute-angled long side which is longer than on the obtuse-angled short side; and
   an external thread structure configured to thread the implant body into a jaw bone, the external thread structure consisting of one lead which extends on a continuous screw line with a constant pitch around the axial line and which is configured to protrude laterally from the body core,
   wherein,
   the lead has a wedge-like shape and comprises a lower side facing the base end, an upper side facing the top end, the upper side and the lower side defining a wedge angle, and
   a bisecting line of the wedge angle and the axial line of the implant body form a tilt angle which is smaller on the acute-angled long side than on the obtuse-angled short side.

2. The jaw implant as recited in claim 1, wherein the tilt angle on the acute-angled long side is <90° and the tilt angle on the obtuse-angled short side is >90°.

3. The jaw implant as recited in claim 1, wherein the wedge angle is constant over a circumference.

4. The jaw implant as recited in claim 1, wherein at least one of the upper side and the lower side are planer.

5. The jaw implant as recited in claim 1, wherein the body core is configured to taper down to the base end.

6. The jaw implant as recited in claim 5, wherein the implant body further comprises an outer radius, and wherein the lead further comprises a radial lead depth which is configured to increase towards the base end such that the outer radius is constant for several turns of the lead.

7. The jaw implant as recited in claim 5, wherein the body core is configured to taper down conically to the base end.

8. The jaw implant as recited in claim 1, wherein the lead further comprises a radial lead depth which is configured to increase towards the base end.

9. The jaw implant as recited in claim 1, wherein the implant body further comprises at least one closed raised support ring disposed at the top end, wherein a ring plane of each of the at least one closed raised support ring is uninterrupted and parallel to the opening plane.

10. The jaw implant as recited in claim 1, wherein the lead further comprises a trapezoidal cross section.

11. A jaw implant comprising an implant body comprising
    a top end configured to fasten a prosthetic implant abutment;
    a base end configured to be inserted into a patient's jaw;
    an axial line;
    an acute-angled long side;
    an obtuse-angled short side;
    a body core;
    an oval opening disposed at the top end, the oval opening comprising an opening edge lying in an opening plane which is inclined with an angle of inclination of 75° to 45° with respect to the axial line so that the implant body has an axial length on the acute-angled long side which is longer than on the obtuse-angled short side;
    at least one closed raised support ring disposed at the top end, wherein a ring plane of each of the at least one closed raised support ring is uninterrupted, is parallel to the opening plane, and is non-perpendicular to the axial line; and
    an external thread structure configured to thread the implant body into a jaw bone, the external thread structure consisting of one lead which extends on a continuous screw line with a constant pitch around the axial line and which is configured to protrude laterally from the body core,
    wherein,
    the lead has a wedge-like shape and comprises a lower side facing the base end, an upper side facing the top end, the upper side and the lower side defining a wedge angle,
    a bisecting line of the wedge angle and the axial line of the implant body form a tilt angle which is smaller on the acute-angled long side than on the obtuse-angled short side,
    the upper side of the lead facing the top end on the obtuse-angled short side is substantially parallel to the opening plane, and
    the lower side of the lead facing the base on the acute-angled long side is substantially parallel to the opening plane.

12. The jaw implant as recited in claim 11, wherein the tilt angle on the acute-angled long side is <90° and the tilt angle on the obtuse-angled short side is >90°.

13. The jaw implant as recited in claim 11, wherein the wedge angle is constant over a circumference.

14. The jaw implant as recited in claim 11, wherein at least one of the upper side and the lower side are planer.

15. The jaw implant as recited in claim 11, wherein the body core is configured to taper down to the base end.

16. The jaw implant as recited in claim 15, wherein the implant body further comprises an outer radius, and wherein the lead further comprises a radial lead depth which is configured to increase towards the base end such that the outer radius is constant for several turns of the lead.

17. The jaw implant as recited in claim 15, wherein the body core is configured to taper down conically to the base end.

18. The jaw implant as recited in claim 11, wherein the lead further comprises a radial lead depth which is configured to increase towards the base end.

19. The jaw implant as recited in claim 11, wherein the lead further comprises a trapezoidal cross section.

\* \* \* \* \*